(12) United States Patent
Park et al.

(10) Patent No.: US 12,122,740 B2
(45) Date of Patent: *Oct. 22, 2024

(54) METHOD OF PREPARING ISOPROPYL ALCOHOL

(71) Applicant: LG CHEM, LTD., Seoul (KR)

(72) Inventors: Sa Eun Park, Daejeon (KR); Tae Woo Kim, Daejeon (KR); Byung Woo Choi, Daejeon (KR); Sung Kyu Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 101 days.

This patent is subject to a terminal disclaimer.

(21) Appl. No.: 17/924,625

(22) PCT Filed: Apr. 29, 2022

(86) PCT No.: PCT/KR2022/006219
§ 371 (c)(1),
(2) Date: Nov. 10, 2022

(87) PCT Pub. No.: WO2022/235025
PCT Pub. Date: Nov. 10, 2022

(65) Prior Publication Data
US 2023/0183156 A1 Jun. 15, 2023

(30) Foreign Application Priority Data
May 6, 2021 (KR) .................. 10-2021-0058712

(51) Int. Cl.
C07C 31/10 (2006.01)
C07C 29/76 (2006.01)
(Continued)

(52) U.S. Cl.
CPC .............. C07C 31/10 (2013.01); C07C 29/76 (2013.01); C07C 29/78 (2013.01); C07C 29/80 (2013.01)

(58) Field of Classification Search
CPC ... C07C 29/04; C07C 29/76–80; C07C 31/10; B01D 3/00; B01D 3/34; B01D 3/343; B01D 3/346; B01D 3/38
See application file for complete search history.

(56) References Cited

U.S. PATENT DOCUMENTS

| 4,469,903 A | 9/1984 | Schmidt |
| 2012/0016164 A1 | 1/2012 | Kohnz et al. |

FOREIGN PATENT DOCUMENTS

| CN | 107501042 A | 12/2017 |
| CN | 111356752 A | 6/2020 |

(Continued)

OTHER PUBLICATIONS

Machine translation of CN 107501042 A, which was published on Dec. 22, 2017 and originally listed on PTO Form SB/08 of IDS filed Nov. 10, 2022, 9 pages.

(Continued)

Primary Examiner — Renee Robinson
(74) Attorney, Agent, or Firm — Bryan Cave Leighton Paisner LLP

(57) ABSTRACT

A method of preparing isopropyl alcohol including: supplying a feed stream including a propylene monomer and water to a reaction unit and reacting the propylene monomer and water to produce a reaction product including isopropyl alcohol, the propylene monomer, and the water; supplying a first discharge stream including a gaseous reaction product and a second discharge stream including a liquid reaction product from the reaction unit to a stripper; and in the stripper, circulating an upper discharge stream including the propylene monomer to the reaction unit and supplying a lower discharge stream including water and isopropyl alcohol to an isopropyl alcohol purification unit, where the first (Continued)

discharge stream is condensed by a first heat exchanger and supplied as a liquid phase to the stripper.

11 Claims, 2 Drawing Sheets

(51) Int. Cl.
*C07C 29/78* (2006.01)
*C07C 29/80* (2006.01)

(56) References Cited

FOREIGN PATENT DOCUMENTS

| | | |
|---|---|---|
| DE | 69605460 | 1/2000 |
| EP | 0 728 721 A2 | 8/1996 |
| EP | 2939995 A1 | 11/2015 |
| EP | 3950654 A1 | 2/2022 |
| JP | 2972496 B2 | 11/1999 |
| JP | 3693404 B2 | 9/2005 |
| JP | WO2017217279 A1 | 4/2019 |
| JP | WO2018-135408 A1 | 11/2019 |
| KR | 10-0219006 B1 | 9/1999 |
| KR | 10-2019-0019060 A | 2/2019 |
| KR | 10-1956407 B1 | 3/2019 |
| KR | 10-2020-0027410 A | 3/2020 |

OTHER PUBLICATIONS

Machine translation of JP 2972496 B2, which was published on Nov. 8, 1999 and originally listed on PTO Form SB/08 of IDS filed Nov. 10, 2022, 8 pages.
Machine translation of JP 3693404 B2, which was published on Sep. 7, 2005 and originally listed on PTO Form SB/08 of IDS filed Nov. 10, 2022, 16 pages.
Machine translation of KR 10-0219006 B1, which was published on Sep. 1, 1999 and originally listed on PTO Form SB/08 of IDS filed Nov. 10, 2022, 13 pages.
Machine translation of KR 10-1956407 B1, which was published on Mar. 8, 2019 and originally listed on PTO Form SB/08 of IDS filed Nov. 10, 2022, 22 pages.
Machine translation of KR 2019-0019060 A, which was published on Feb. 26, 2019 and originally listed on PTO Form SB/08 of IDS filed Nov. 10, 2022, 18 pages.
Machine translation of KR 2020-0027410 A, which was published on Mar. 12, 2020 and originally listed on PTO Form SB/08 of IDS filed Nov. 10, 2022, 20 pages.
Machine translation of WO 2018/135408 A1, which was published on Jul. 26, 2018 and originally listed on PTO Form SB/08 of IDS filed Nov. 10, 2022, 37 pages.

[FIG. 1]
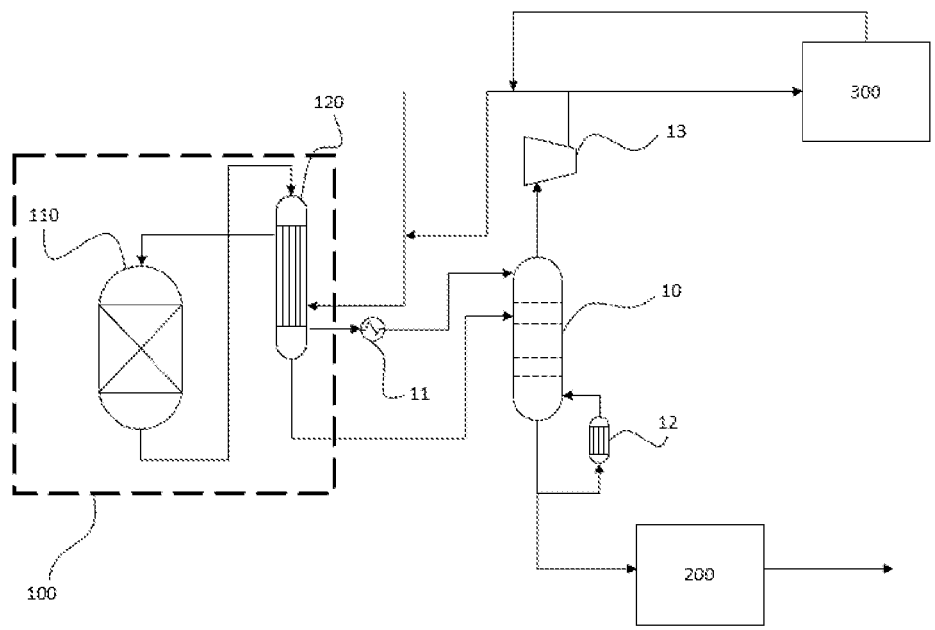
[FIG. 2]
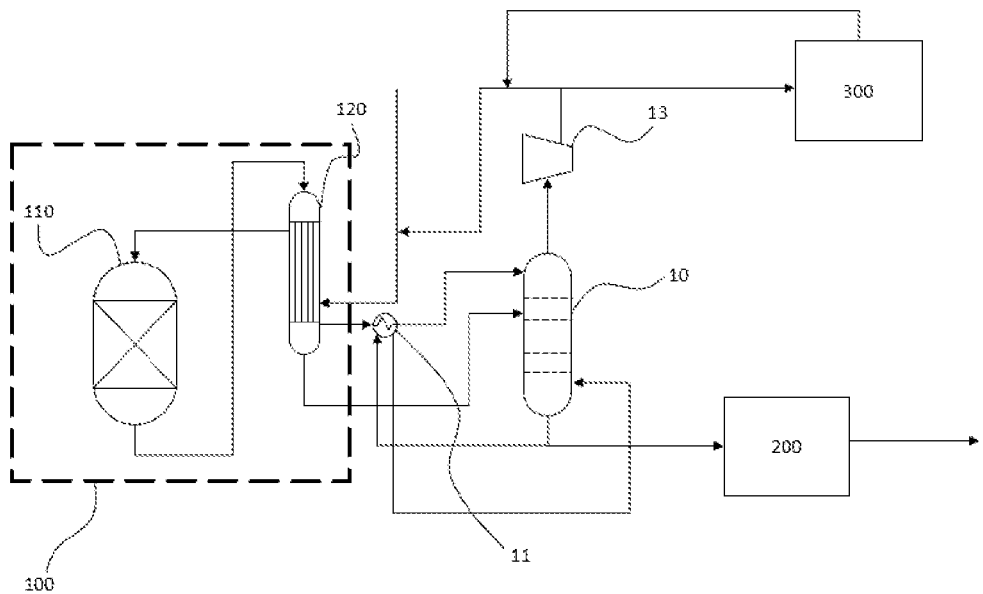

【FIG. 3】
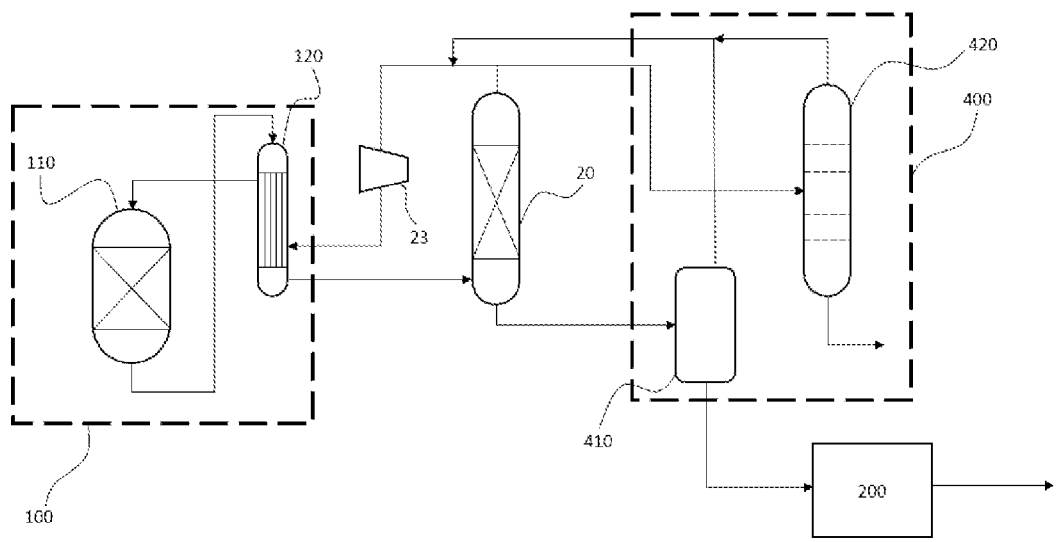
-PRIOR ART-
【FIG. 4】
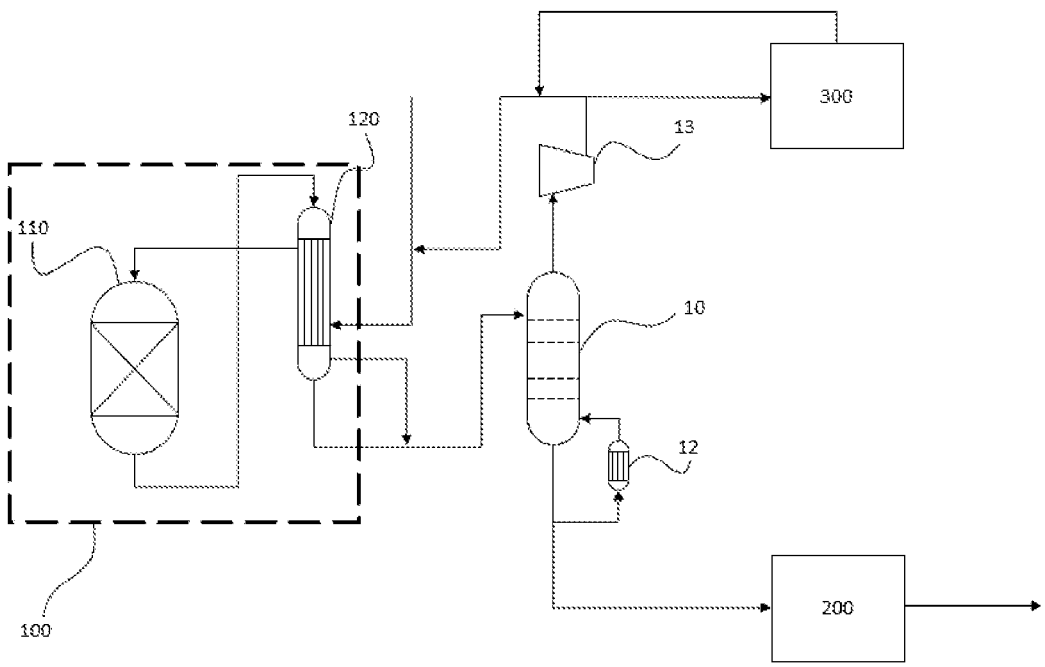
-PRIOR ART-

METHOD OF PREPARING ISOPROPYL ALCOHOL

CROSS-REFERENCE TO RELATED APPLICATIONS

The present application is a US national phase of international application No. PCT/KR2022/006219, filed on Apr. 29, 2022, and claims the benefit of priority to Korean Patent Application No. 10-2021-0058712, filed on May 6, 2021, the entire contents of which are incorporated as if fully set forth herein in their entirety.

TECHNICAL FIELD

The present invention relates to a method of preparing isopropyl alcohol, and more particularly, to a method of reducing the number of devices in separating high purity isopropyl alcohol from a reaction product of an isopropyl alcohol preparation process and effectively recovering an unreacted product, thereby reducing costs of devices and energy.

BACKGROUND

Isopropyl alcohol (IPA) is used for various purposes including as a cleaning agent or the like, in the electronic industry, such as in the manufacture of a semiconductor or a liquid crystal display (LCD).

In a process of preparing isopropyl alcohol, for example, propylene and water are used as raw material components. The propylene and water react to produce isopropyl alcohol.

The reaction product of the isopropyl alcohol preparation process includes isopropyl alcohol, an unreacted propylene monomer, and unreacted water. Isopropyl alcohol is separated and recovered from the reaction product of the isopropyl alcohol preparation process, and the unreacted propylene monomer is recovered and reused in the isopropyl alcohol preparation process.

Conventionally, an absorption column is used for separating the isopropyl alcohol and the unreacted propylene monomer from the reaction product of the isopropyl alcohol preparation process. Specifically, the isopropyl alcohol preparation process is a gaseous reaction, in which the gaseous reaction product produced is supplied to a lower stage of an absorption column, isopropyl alcohol in the reaction product is dissolved using water as a solvent and separated into a lower stage of the absorption column, and a stream including the propylene monomer is separated into an upper portion. However, when the conventional method is used, the separation efficiency of the absorption column is low and about 1 wt % to 5 wt % of the propylene monomer flows into a lower portion of the absorption column, and thus, since a flash drum, a distillation column, and the like are further required for recovering the monomer, the process becomes complicated and investment costs and equipment maintenance costs are increased. In addition, much energy is used in separating water and isopropyl alcohol and recovering water in the latter stage of the absorption column because 25 wt % or more of water relative to the flow rate of the reaction product supplied to the absorption column is needed. In addition, inert gas present in the propylene monomer supplied to a reactor is not removed and is accumulated in the process because there is no inert gas removal unit, and thus, a high-purity propylene monomer should be used.

To solve these problems, a study was conducted on mixing a gaseous reaction product and a liquid reaction product which are discharged after condensing a gaseous reaction product in the isopropyl alcohol preparation process and then supplying the mixture to a first stage of a stripper to separate isopropyl alcohol and a propylene monomer. However, isopropyl alcohol and water in the gaseous reaction product which is not condensed and is introduced to the stripper are discharged in a gaseous state to an upper portion of the stripper in this case as well, and because isopropyl alcohol and water included in the liquid reaction product do not pass through a rectifying unit, most of them are discharged to the upper portion.

SUMMARY

To solve the problems mentioned above, an objective of the present invention is to provide a method of reducing costs of devices and energy by reducing the number of devices used for effectively separating isopropyl alcohol and a propylene monomer from a reaction product of an isopropyl alcohol preparation process.

That is, the present invention may provide a method of producing a reaction product in a reaction unit and separating the reaction product into a gaseous first discharge stream and a liquid second discharge stream and supplying each of them to a stripper, thereby preventing outflow of a propylene monomer into a lower portion of a stripper and easily recovering a propylene monomer recovered in an upper portion to a reactor in the reaction unit.

In one general aspect, a method of preparing isopropyl alcohol includes: supplying a feed stream including a propylene monomer and water to a reaction unit and performing a reaction to produce a reaction product including isopropyl alcohol, the propylene monomer, and the water; supplying a first discharge stream including a gaseous reaction product and a second discharge stream including a liquid reaction product which are discharged from the reaction unit to a stripper, respectively; and in the stripper, circulating an upper discharge stream including the propylene monomer to the reaction unit and supplying a lower discharge stream including water and isopropyl alcohol to an isopropyl alcohol purification unit, wherein the first discharge stream is condensed by a first heat exchanger and supplied as a liquid phase to the stripper.

According to the method of preparing isopropyl alcohol of the present invention, a reaction product in an isopropyl alcohol preparation process is separated into a gaseous first discharge stream and a liquid second discharge stream which are supplied to a stripper, respectively, thereby increasing separation efficiency in the stripper.

In addition, since a lower discharge stream from the stripper and the first discharge stream may exchange heat, energy for heating the lower discharge stream from the stripper may be reduced.

In addition, the outflow of the propylene monomer into the lower portion of a stripper is prevented so that a complicated latter stage process for separating a propylene monomer from the lower discharge stream from the stripper is not required, and costs of devices and equipment maintenance therefrom may be reduced.

In addition, the content of isopropyl alcohol in the upper discharge stream from the stripper which is circulated to a reactor is minimized to promote a forward reaction of an equilibrium reaction, thereby increasing the production of isopropyl alcohol.

BRIEF DESCRIPTION OF DRAWINGS

FIGS. 1 and 2 are process flow diagrams of a method of preparing isopropyl alcohol according to the Examples of the present invention.

FIGS. 3 and 4 are process flow diagrams of a method of preparing isopropyl alcohol according to the Comparative Examples.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention may refer to a fluid flow in a process, or may refer to a fluid itself flowing in a pipe. Specifically, the stream may refer to both a fluid itself flowing in a pipe connecting each device and a fluid flow. In addition, the fluid may refer to a gas or a liquid. Herein, a case in which a solid component is included in the fluid is not excluded.

Hereinafter, the present invention will be described in more detail with reference to FIGS. 1 and 2, for better understanding of the present invention.

According to the present invention, a method of preparing isopropyl alcohol is provided. The isopropyl alcohol may be produced by a vapor phase reaction of a propylene monomer and water. Specifically, a feed stream including a propylene monomer and water is supplied to a reaction unit 100, and a reaction product produced in the reaction unit 100 may include isopropyl alcohol, an unreacted propylene monomer, and unreacted water. The isopropyl alcohol is separated from the reaction product and recovered, and the unreacted propylene monomer is recovered and reused in the isopropyl alcohol preparation process.

Conventionally, an absorption column is used for separating the isopropyl alcohol and the unreacted propylene monomer from the reaction product. Specifically, the isopropyl alcohol preparation process is a gaseous reaction, in which the reaction product produced is supplied to a lower stage of the absorption column, isopropyl alcohol in the reaction product is dissolved using a solvent and separated into a lower portion of the absorption column, and a stream including the propylene monomer is separated into an upper portion. However, when the conventional method is used, the separation efficiency of the absorption column is low and about 1 wt % to 5 wt % of the propylene monomer flows into a lower portion of the absorption column, and thus, the process becomes complicated and investment costs and equipment maintenance costs are increased because a flash drum, a distillation column, and the like are further required for recovering the monomer. In addition, much energy is used in separating water and isopropyl alcohol and recovering water in the latter stage of the absorption column because 25 wt % or more of the solvent relative to the flow rate of the reaction product supplied to the absorption column is needed. In addition, inert gas present in the propylene monomer supplied to the reactor is not removed and accumulates in the process because there is no inert gas removal unit, and thus, a high-purity propylene monomer should be used.

To solve these problems, mixing a gaseous reaction product and a liquid reaction product which are discharged after condensing a gaseous reaction product in the isopropyl alcohol preparation process and then supplying the mixture to a first stage of a stripper to separate isopropyl alcohol and a propylene monomer was studied. However, even in this case, isopropyl alcohol and water in the gaseous reaction product which is not condensed and is introduced to the stripper are discharged in a gaseous state to an upper portion of the stripper, and because isopropyl alcohol and water included in the liquid reaction product do not pass through a rectifying unit, most of them are discharged to the upper portion.

To solve the conventional problems described above, it is intended in the present invention to provide a method of maximizing the separation efficiency of isopropyl alcohol and the propylene monomer to simplify the conventional complicated process, and also, decreasing the number of devices and the amount of energy used, required in the process.

According to an exemplary embodiment of the present invention, a method of preparing isopropyl alcohol includes: supplying a feed stream including a propylene monomer and water to a reaction unit 100 and performing a reaction to produce a reaction product including isopropyl alcohol, the propylene monomer, and the water; supplying a first discharge stream including a gaseous reaction product and a second discharge stream including a liquid reaction product which are discharged from the reaction unit 100 to a stripper 10, respectively; and in the stripper 10, circulating an upper discharge stream including the propylene monomer to the reaction unit 100 and supplying a lower discharge stream including water and isopropyl alcohol to an isopropyl alcohol purification unit 200, wherein the first discharge stream is condensed by a first heat exchanger 11 and supplied as a liquid phase to the stripper 10.

A mole ratio of water to the propylene monomer included in the feed stream supplied to the reaction unit 100 may be 0.3 to 0.5, 0.35 to 0.5, or 0.35 to 0.45. When the mole ratio of water to the propylene monomer in the feed stream supplied to the reaction unit 100 satisfies the above range, a forward reaction of an equilibrium reaction is promoted and progression of a reverse reaction is prevented to increase the production of isopropyl alcohol.

The reaction unit 100 may include a reactor 110 and one or more second heat exchangers. Specifically, the feed stream including the propylene monomer and water may be supplied to the reactor 110 of the reaction unit 100, and may react in a gaseous phase in the reactor 110 to produce a reaction product.

An operation pressure of the reactor 110 may be, for example, 30 kg/cm$^2$·g to 50 kg/cm$^2$·g, 35 kg/cm$^2$·g to 50 kg/cm$^2$·g, or 35 kg/cm$^2$·g to 45 kg/cm$^2$·g. When the reactor 110 is operated in these pressure ranges, isopropyl alcohol may be produced by a gaseous reaction using the propylene monomer and water.

By reacting the propylene monomer and water in a gaseous phase in the reactor 110, a gaseous reaction product may be discharged from the reactor 110. Here, the temperature of the gaseous reaction product discharged from the reactor 110 may be, for example, 200° C. to 220° C., 205° C. to 220° C., or 205° C. to 215° C.

According to an exemplary embodiment of the present invention, the gaseous reaction product discharged from the reactor 110 passes through one or more second heat exchangers, and a part of the product is condensed into a liquid reaction product and a remaining product may be present as the gaseous reaction product. As an example, the gaseous reaction product discharged from the reactor 110 passes through a second heat exchange 120, and may be separated into a first discharge stream including a gaseous reaction product and a second discharge stream including a liquid reaction product. Here, the first discharge stream and the second discharge stream may be separated and discharged by a separate pipe formed in the second heat exchanger 120, or may be separated by a gas-liquid separation device installed in the latter stage of the second heat exchanger 120.

According to an exemplary embodiment of the present invention, the gaseous reaction product discharged from the reactor 110 may exchange heat with a feed stream supplied to the reactor 110 in one or more second heat exchangers. Specifically, the gaseous reaction product discharged from the reactor 110 may be partly condensed while passing through one or more second heat exchangers, and the feed stream may be heated while passing through the one or more second heat exchangers before being supplied to the reactor 110. The temperature of the feed stream before passing through the one or more second heat exchangers may be, for example, 90° C. to 130° C., 100° C. to 120° C., or 105° C. to 115° C. In addition, the temperature of the feed stream which has passed through the one or more second heat exchangers may be, for example, 170° C. to 210° C., 180° C. to 200° C., or 185° C. to 195° C. In addition, the temperature of the first discharge stream and the second discharge stream which have passed through the one or more second heat exchangers may be, for example, 105° C. to 150° C., 110° C. to 140° C., or 115° C. to 140° C.

By exchanging heat between the gaseous reaction product stream discharged from the reactor 110 and the feed stream, discharge from the reactor 110 may be separated into a first discharge stream including a gaseous reaction product and a second discharge stream including a liquid reaction product, and also the feed stream may be preheated and supplied to the reactor 110. Thus, energy for heating the feed stream supplied to the reactor 110 may be reduced, and the temperature and the composition of the first discharge stream and the second discharge stream may be controlled to increase separation efficiency of a subsequent separation process using a stripper.

According to an exemplary embodiment of the present invention, the first discharge stream may include 85 wt % to 95 wt % of the propylene monomer, 4 wt % to 8 wt % of isopropyl alcohol, and 1 wt % to 5 wt % of water. Specifically, it is recognized that the first discharge stream includes a very high content of the propylene monomer and very low contents of isopropyl alcohol and water.

In addition, the second discharge stream may include 1 wt % to 10 wt % of the propylene monomer, 5 wt % to 15 wt % of isopropyl alcohol, and 80 wt % to 90 wt % of water. Specifically, it is recognized that the second discharge stream includes a very low content of the propylene monomer and very high contents of water. The content of isopropyl alcohol included in the second discharge stream may be higher than the content of isopropyl alcohol included in the first discharge stream.

According to an exemplary embodiment of the present invention, a ratio of the flow rate of the first discharge stream to the flow rate of the second discharge stream, discharged from the reaction unit 100, may be 5 to 11, 6 to 10, or 7 to 9. As described above, in the process of exchanging heat between the gaseous reaction product stream discharged from the reactor 110 and the feed stream in one or more second heat exchangers, the gaseous reaction product stream discharged from the reactor 110 is cooled to a temperature of 105 to 150° C., thereby controlling the ratio of the flow rate of the first discharge stream to the flow rate of the second discharge stream to 5 to 11. Herein, the "flow rate" may refer to a flow of a weight per unit hour. As a specific example, the unit of the flow rate may be ton/hr.

According to an exemplary embodiment of the present invention, the first discharge stream and the second discharge stream may be supplied to the stripper 10 as respective streams, and separated. Specifically, an upper discharge stream including the propylene monomer and a lower discharge stream including water and isopropyl alcohol from the stripper 10 may be separated.

The first discharge stream including a gaseous reaction product may be condensed by the first heat exchanger 11 and supplied to the stripper 10 as a liquid phase. For example, in the first heat exchanger 11, a separate refrigerant is used or heat exchange with a stream in the process is performed, thereby condensing the first discharge stream. If necessary, a cooler may be further used in addition to the first heat exchanger 11 to condense the first discharge stream and supply it as a liquid phase to the stripper 10. In this case, when the first discharge stream is firstly condensed by the first heat exchanger 11 and secondarily cooled in the cooler, the refrigerant used in the cooler may be replaced with low-priced coolant, and the amount of coolant used may be minimized.

Since the first discharge stream and the second discharge stream have different components, the supply stages of the first discharge stream and the second discharge stream supplied to the stripper 10 are controlled, thereby increasing the separation efficiency of the isopropyl alcohol and the propylene monomer.

According to an exemplary embodiment of the present invention, the first discharge stream may be supplied to an upper part of the stripper 10. For example, the first discharge stream is condensed by the first heat exchanger 11, and the condensed first discharge stream may be supplied to a first stage of the stripper 10.

In comparison, the second discharge stream may be supplied to the stripper at a position 10 lower than the upper part of the stripper to which the first discharge stream is supplied. For example, the second discharge stream may be supplied to a stage at 10% to 50% or 15% to 35% of the theoretical number of stages of the stripper 10. For example, when the theoretical number of stages (total stages) of the stripper 10 is 100, the top stage may be a first stage and a bottom stage may be a 100th stage, and the stage at 3% to 10% of the theoretical number of stages of the stripper 10 may be a third stage to a 10th stage of the stripper 10. Since the second discharge stream may have a lower content of the propylene monomer and higher contents of isopropyl alcohol and water than the first discharge stream, the second discharge stream is supplied to the stages in the above range of the stripper 10, thereby reducing the operation cost of a reboiler 12 installed in the lower portion of the stripper 10, and securing a rectifying unit in the stripper 10 to increase the separation efficiency of isopropyl alcohol and water.

According to an exemplary embodiment of the present invention, the operation pressure of the stripper 10 may be 0 kg/cm²·g to 5 kg/cm²·g, 1 kg/cm²·g to 4 kg/cm²·g, or 1 kg/cm²·g to 3 kg/cm²·g. By operating the stripper 10 in the above ranges, the high purity propylene monomer may be separated from the upper discharge stream.

As such, by controlling the supply conditions to the stripper 10 of the first discharge stream and the second discharge stream, the operating conditions of the stripper 10, and the like, the upper discharge stream from the stripper 10 may be circulated to the reactor 110 of the reaction unit 100 without further purification. More specifically, a problem of promoting a reverse reaction of an equilibrium reaction to decrease the production of isopropyl alcohol when isopropyl alcohol is circulated to the reactor 110 may be solved by minimizing the content of isopropyl alcohol in the upper discharge stream from the stripper 10. In addition, no propylene monomer is present in the lower discharge stream from the stripper 10, so that the lower discharge stream from the stripper 10 may be supplied to an isopropyl alcohol purification unit 200 without a complicated latter stage process for recovering propylene from the lower discharge stream.

According to an exemplary embodiment of the present invention, a part branched from the upper discharge stream from the stripper 10 is supplied to an inert gas removal unit 300, and after removing an inert gas component in the inert gas removal unit 300, the stream may be circulated to the reaction unit 100. Specifically, in the isopropyl alcohol preparation process performed as a gaseous reaction, a part of inert gas may be included in the propylene monomer introduced as a reactant. The inert gas may include, for example, one or more selected from the group consisting of hydrocarbons having 2 or 3 carbon atoms, and as a specific example, the inert gas may include one or more selected from the group consisting of ethane and propane. As such, when a part branched from the upper discharge stream from the stripper 10 is supplied to the inert gas removal unit 300 to remove inert gas and then circulated to the reaction unit 100, the inert gas is not accumulated in the process, and the productivity of isopropyl alcohol may be improved without using a high-purity propylene monomer.

According to an exemplary embodiment of the present invention, the upper discharge stream from the stripper 10 may exchange heat with the gaseous reaction product stream discharged from the reactor 110 while passing through one or more second heat exchangers of the reaction unit 100, and then may be supplied to the reactor 110. Here, the temperature of the upper discharge stream from the stripper 10 may be, for example, −10° C. to 30° C., 5° C. to 30° C., or 10° C. to 20° C. The upper discharge stream from the stripper 10 may be mixed with the feed stream and pass through one or more second heat exchangers of the reaction unit 100.

According to an exemplary embodiment of the present invention, the lower discharge stream from the stripper 10 may be a stream including isopropyl alcohol and water but no propylene monomer. Here, the temperature of the lower discharge stream from the stripper 10 may be, for example, 40° C. to 110° C., 60° C. to 110° C., or 80° C. to 90° C. As such, a part of the lower discharge stream from the stripper 10 at a low temperature may be supplied to a reboiler 12, heated in the reboiler 12, and then refluxed to the stripper 10. In addition, the rest of the lower discharge stream from the stripper 10 which is not supplied to the reboiler 12 may be supplied to the isopropyl alcohol purification unit 200.

According to an exemplary embodiment of the present invention, the part of the lower discharge stream from the stripper 10 at a low temperature may be supplied to the first heat exchanger 11 and the residual stream may be supplied to the isopropyl alcohol purification unit 200. The part of the lower discharge stream from the stripper 10 which has exchanged heat with the first discharge stream in the first heat exchanger 11 may be heated using condensed heat of the first discharge stream, and a heated part of the lower discharge stream from the stripper 10 may be refluxed to the stripper 10.

The rest of the lower discharge stream from the stripper 10 which is not supplied to the first heat exchanger 11 is supplied to the isopropyl alcohol purification unit 200 to separate high-purity isopropyl alcohol from which water has been removed. Here, water separated in the isopropyl alcohol purification unit 200 may be supplied to the reactor 110 and reused, and in this case, impurities such as a propylene monomer or isopropyl alcohol are not included, and thus, it may be easy to control a mole ratio of water to the propylene monomer in preparing isopropyl alcohol in the reactor 110.

However, as shown in FIG. 3, when a conventional absorption column 20 is used instead of the stripper 10 of the present invention, the reaction product is supplied to a lower stage of the absorption column, isopropyl alcohol in the reaction product is dissolved using water as a solvent and separated from the lower portion of the absorption column 20, and a stream including the propylene monomer is separated from the upper portion. Further, separation efficiency in the absorption column 20 is low, so that the propylene monomer flows into the lower discharge stream from the absorption column 20, and thus, in order to recover it, a gas purification unit 400 requiring a plurality of devices is needed. Specifically, the gas purification unit 400 further requires a flash drum 410, a distillation column 420, and the like for recovering an unreacted propylene monomer, which causes the process to be complicated and investment costs, equipment maintenance costs, and energy costs to increase.

In addition, much energy is used for separating water and isopropyl alcohol from the latter stage of the absorption column 20 because 25% or more water relative to the flow rate of the reaction product supplied to the absorption column 20 is needed. Specifically, much energy is further needed for separating water and isopropyl alcohol from the isopropyl alcohol purification unit 200.

According to an exemplary embodiment of the present invention, devices such as a distillation column, a condenser, a reboiler, a valve, a pump, a separator, and a mixer may be further installed and used in the method of preparing isopropyl alcohol, if needed.

Hereinabove, the method of preparing isopropyl alcohol according to the present invention has been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the method of preparing isopropyl alcohol according to the present invention.

Hereinafter, the present invention will be described in more detail with reference to the Examples. However, the following Examples are provided for illustrating the present invention, and it would be apparent to a person skilled in the art that various modifications and alterations may be made without departing from the scope and spirit of the present invention and the scope of the present invention is not limited thereto.

EXAMPLES

Example 1

As shown in the process flow diagram illustrated in FIG. 1, a reaction product including isopropyl alcohol (IPA) was prepared, and isopropyl alcohol was separated from the reaction product.

Specifically, a feed stream was supplied at a flow rate of 10 ton/hr to a reactor 110 operating at a pressure of 40 kg/cm²·g, and a mole ratio of water (H₂O) to a propylene monomer (PP) in the feed stream was controlled to 0.4 and ethane and propane were included as inert gas. At this time, the feed stream passed through a second heat exchanger 120 and then was supplied to a reactor 110.

The gaseous reaction product stream discharged from the reactor 110 was separated into a first discharge stream and a second discharge stream while passing through a second heat exchanger 120 and discharged, and the first discharge stream was condensed in a first heat exchanger 11 and then supplied to a first stage of a stripper 10. In addition, the second discharge stream was supplied to a fifth stage of the stripper 10.

The stripper 10 was operated at an operating pressure of 2 kg/cm²·g, the upper discharge stream from the stripper 10 was compressed using a compressor 13, mixed with the feed stream, and circulated to the reactor 110, and a part branched from the upper discharge stream from the stripper 10 was supplied to an inert gas removal unit 300 to remove ethane and propane, and then circulated to the reactor 110. In addition, a part of the lower discharge stream from the stripper 10 was supplied to a reboiler 12 and then refluxed, and a residual stream was supplied to an isopropyl alcohol purification unit 200 to obtain isopropyl alcohol from which water was removed. At this time, the total number of stages of the stripper 10 was 19.

The flow rate, the temperature, and the components of the first discharge stream and the second discharge stream and the supply stages of the stripper 10 are shown in Table 1. In addition, the flow rate, the temperature, and the components of the upper discharge stream and the lower discharge stream from the stripper 10 and the amount of steam used for heating the lower discharge stream from the stripper 10 are shown in Table 2.

Example 2

As shown in the process flow diagram illustrated in FIG. 2, a reaction product including isopropyl alcohol (IPA) was prepared, and isopropyl alcohol was separated from the reaction product.

Specifically, a feed stream was supplied at a flow rate of 10 ton/hr to the reactor 110 operated at a pressure of 40 kg/cm²·g, and the mole ratio of water to the propylene monomer in the feed stream was controlled to 0.4. The feed stream was passed through a second heat exchanger 120 and then was supplied to a reactor 110.

The gaseous reaction product stream discharged from the reactor 110 was separated into a first discharge stream and a second discharge stream while passing through a second heat exchanger 120 and discharged, and the first discharge stream was supplied to the first heat exchanger 11, condensed by heat exchange with a part of the lower discharge stream from the stripper 10, and supplied to the first stage of the stripper 10. In addition, the second discharge stream was supplied to a fifth stage of the stripper 10. If necessary, a separate condenser was installed to further condense an uncondensed first discharge stream using a coolant.

The stripper 10 was operated at an operating pressure of 2 kg/cm²·g, the upper discharge stream from the stripper 10 was compressed to the pressure of the reactor 110 using a compressor 13, mixed with the feed stream, and circulated to the reactor 110, and a part branched from the upper discharge stream from the stripper 10 was supplied to an inert gas removal unit 300 to remove ethane and propane, and then circulated to the reactor 110. In addition, a part of the lower discharge stream from the stripper 10 was supplied to the first heat exchanger 11 and then refluxed, and a residual stream was supplied to an isopropyl alcohol purification unit 200 to obtain isopropyl alcohol from which water was removed. At this time, the total number of stages of the stripper 10 was 19.

The resulting flow rate, the temperature, and the components of the first discharge stream and the second discharge stream and the supply stages of the stripper 10 are shown in Table 1. In addition, the flow rate, the temperature, and the components of the upper discharge stream and the lower discharge stream from the stripper 10 and the amount of steam used for heating the lower discharge stream from the stripper 10 are shown in Table 2.

Example 3

Isopropyl alcohol was prepared in the same manner as in Example 2, except that the temperatures of the first discharge stream and the second discharge stream were controlled to 110° C.

The resulting flow rate, the temperature, and the components of the first discharge stream and the second discharge stream and the supply stages of the stripper 10 are shown in Table 1. In addition, the flow rate, the temperature, and the components of the upper discharge stream and the lower discharge stream from the stripper 10 and the amount of steam used for heating the lower discharge stream from the stripper 10 are shown in Table 2.

Example 4

Isopropyl alcohol was prepared in the same manner as in Example 2, except that the supply stage of the second discharge stream was adjusted to a 3rd stage.

The resulting flow rate, the temperature, and the components of the first discharge stream and the second discharge stream and the supply stages of the stripper 10 are shown in Table 1. In addition, the flow rate, the temperature, and the components of the upper discharge stream and the lower discharge stream from the stripper 10 and the amount of steam used for heating the lower discharge stream from the stripper 10 are shown in Table 2.

Example 5

Isopropyl alcohol was prepared in the same manner as in Example 2, except that the supply stage of the second discharge stream was adjusted to a 10th stage.

The resulting flow rate, the temperature, and the components of the first discharge stream and the second discharge stream and the supply stages of the stripper 10 are shown in Table 1. In addition, the flow rate, the temperature, and the components of the upper discharge stream and the lower discharge stream from the stripper 10 and the amount of steam used for heating the lower discharge stream from the stripper 10 are shown in Table 2.

Comparative Examples

Comparative Example 1

As shown in the process flow diagram illustrated in FIG. 3, a reaction product including isopropyl alcohol (IPA) was prepared, and isopropyl alcohol was separated from the reaction product.

Specifically, a feed stream was supplied at a flow rate of 10 ton/hr to the reactor 110 operated at a pressure of 40 kg/cm²·g, and the mole ratio of water to the propylene monomer in the feed stream was controlled to 0.4. The feed stream was passed through a second heat exchanger 120 and then was supplied to a reactor 110.

The reaction product stream discharged from the reactor 110 was condensed while passing through the second heat exchanger 120, and then was supplied to the 20$^{th}$ stage of an absorption column 20. In this Comparative Example, the total number of stages of the absorption column 20 was 20.

Isopropyl alcohol in the reaction product stream was absorbed using water supplied to an upper stage of the absorption column 20, thereby separating into an upper discharge stream including a propylene monomer and a lower discharge stream including water and isopropyl alcohol.

The upper discharge stream from the absorption column 20 was circulated to the reactor 110 using a compressor 23, and a part branched from the upper discharge stream from the absorption column 20 was supplied to a distillation column 420 of a gas purification unit 400 and was further separated into water with isopropyl alcohol and the propylene monomer. In addition, the lower discharge stream from the absorption column 20 was supplied to a flash drum 410 of the gas purification unit 400 and was further separated into water with isopropyl alcohol and the propylene monomer.

The stream including propylene separated from the gas purification unit 400 was circulated to the reactor 110, and the stream including isopropyl alcohol and water was supplied to an isopropyl alcohol purification unit 200 to obtain isopropyl alcohol from which water was removed.

It was confirmed that the flow rate of the reaction product stream was 10 ton/hr, its temperature was 124° C., its components were 80.8 wt % of the propylene monomer (PP), 6.3 wt % of isopropyl alcohol, and 12.9 wt % of water (H$_2$O). In addition, the flow rate, the temperature, and the components of the upper discharge stream and the lower discharge stream of the absorption column 20 are shown in Table 2.

Comparative Example 2

As shown in the process flow diagram illustrated in FIG. 4, a reaction product including isopropyl alcohol (IPA) was prepared, and isopropyl alcohol was separated from the reaction product.

Specifically, a feed stream was supplied at a flow rate of 10 ton/hr to the reactor 110 operated at a pressure of 40 kg/cm²·g, and the mole ratio of water to the propylene monomer in the feed stream was controlled to 0.4. The feed stream was passed through a second heat exchanger 120 and then was supplied to a reactor 110.

The gaseous reaction product stream discharged from the reactor 110 was supplied to the first stage of the stripper 10 by mixing the separated first discharge stream and second discharge stream while passing through a second heat exchanger 120.

The stripper 10 was operated at an operating pressure of 2 kg/cm²·g, the upper discharge stream from the stripper 10 was compressed to the pressure of the reactor 110 using a compressor 13, mixed with the feed stream, and circulated to the reactor 110, and a part branched from the upper discharge stream from the stripper 10 was supplied to an inert gas removal unit 300 to remove ethane and propane, and then circulated to the reactor 110. In addition, a part of the lower discharge stream from the stripper 10 was supplied to a reboiler 12 and then refluxed, and a residual stream was supplied to an isopropyl alcohol purification unit 200 to obtain isopropyl alcohol from which water was removed. At this time, the total number of stages of the stripper 10 was 19.

The resulting flow rate, the temperature, and the components of the first discharge stream and the second discharge stream and the supply stages of the stripper 10 are shown in Table 1. In addition, the flow rate, the temperature, and the components of the upper discharge stream and the lower discharge stream from the stripper 10 and the amount of steam used for heating the lower discharge stream from the stripper 10 are shown in Table 2.

TABLE 1

| | | Example 1 | Example 2 | Example 3 | Example 4 | Example 5 | Comparative Example 2 |
|---|---|---|---|---|---|---|---|
| Flow rate of first discharge stream (ton/hr) | | 9 | 9 | 9 | 9 | 9 | 9 |
| Flow rate of second discharge stream (ton/hr) | | 1 | 1 | 1 | 1 | 1 | 1 |
| Temperature of first discharge stream (° C.) | | 124 | 124 | 110 | 124 | 124 | 124 |
| Temperature of second discharge stream (° C.) | | 124 | 124 | 110 | 124 | 124 | 124 |
| Supply stage of first discharge stream | | 1st stage | 1st stage | 1st stage | 1st stage | 1st stage | 1st stage |
| Supply stage of second discharge stream | | 5th stage | 5th stage | 5th stage | 3rd stage | 10th stage | 1st stage |
| First discharge stream | PP (wt %) | 91.0 | 91.0 | 92.5 | 91.0 | 91.0 | 91.0 |
| | IPA (wt %) | 6.2 | 6.2 | 5.8 | 6.2 | 6.2 | 6.2 |
| | H$_2$O (wt %) | 2.8 | 2.8 | 1.7 | 2.8 | 2.8 | 2.8 |
| Second discharge stream | PP (wt %) | 5.8 | 5.8 | 5.0 | 5.8 | 5.8 | 5.8 |
| | IPA (wt %) | 6.8 | 6.8 | 9.7 | 6.8 | 6.8 | 6.8 |
| | H$_2$O (wt %) | 87.4 | 87.4 | 85.3 | 87.4 | 87.4 | 87.4 |

TABLE 2

|  |  | Example 1 | Example 2 | Example 3 | Example 4 | Example 5 | Comparative Example 1 | Comparative Example 2 |
|---|---|---|---|---|---|---|---|---|
| Flow rate of upper discharge stream (ton/hr) | | 8 | 8 | 7.5 | 8 | 8 | 8 | 9 |
| Flow rate of lower discharge stream (ton/hr) | | 2 | 2 | 2.5 | 2 | 2 | 4 | 1 |
| Temperature of upper discharge stream (° C.) | | 15 | 15 | −6 | 15 | 15 | 98 | 76 |
| Temperature of lower discharge stream (° C.) | | 86 | 86 | 83 | 86 | 86 | 96 | 134 |
| Upper discharge stream | PP (wt %) | 99.6 | 99.6 | 99.9 | 99.6 | 99.5 | 97.6 | 87.2 |
|  | IPA (wt %) | 0.3 | 0.3 | 0.1 | 0.3 | 0.4 | 1.1 | 6.48 |
|  | $H_2O$ (wt %) | 0.1 | 0.1 | 0 | 0.1 | 0.1 | 1.3 | 6.0 |
| Lower discharge stream | PP (wt %) | 0 | 0 | 12.0 | 0 | 0.01 | 3.9 | 0 |
|  | IPA (wt %) | 32.0 | 32.0 | 28.8 | 32.0 | 31.96 | 11.6 | 0 |
|  | $H_2O$ (wt %) | 68.0 | 68.0 | 59.2 | 68.0 | 68.03 | 84.5 | 100 |
| Amount of steam used (%) | | 100% | 0% | 0% | 0% | 0% | — | 36.8% |

In Table 2, the amounts of steam used for heating the lower discharge stream from the stripper 10 in Examples 1 to 5 and Comparative Example 2 were measured, respectively, and were converted into a percentage of the amount of steam used for heating the lower discharge stream from the stripper 10 in Example 1, thereby indicating the amount of steam used.

As shown in Tables 1 and 2, it was confirmed that the upper discharge stream from the stripper 10 had the controlled contents of isopropyl alcohol and water, and the lower discharge stream from the stripper 10 had the controlled content of the propylene monomer in Examples 1 to 5, in which the first discharge stream and the second discharge stream which were discharged from the reaction unit 100 are supplied as respective streams to the stripper 10 by the method according to the present invention. In particular, separation in the stripper 10 occurred effectively in Examples 1, 2, and 4, in which the second discharge stream was supplied to the stage at 15% to 35% of the total number of stages of the stripper 10, and the temperatures of the first discharge stream and the second discharge stream were controlled to 115° C. to 140° C., and thus, it was confirmed that there was no propylene monomer in the lower discharge stream from the stripper 10.

In addition, in Examples 2 to 5, isopropyl alcohol was prepared in the same manner as in Example 1, except that heat was exchanged between the lower discharge stream from the stripper 10 and the first discharge stream, and it was confirmed that there was no need to use separate steam for heating the lower discharge stream from the stripper 10.

In comparison, in Comparative Example 1, which is a conventional method of preparing isopropyl alcohol and in which the absorption column 20 was used instead of the stripper 10, about 4 wt % of the propylene monomer was present in the lower discharge stream from the absorption column 20 to essentially require the gas purification unit 400, and it was recognized that a flash drum, a distillation column, and the like were further needed for recovering an unreacted propylene monomer from the gas purification unit 400.

In addition, in Comparative Example 2, in which isopropyl alcohol was prepared in the same manner as in Example 1, but the first discharge stream and the second discharge stream were mixed and supplied to the first stage of the stripper 10, the amount of steam used for heating the lower discharge stream from the stripper 10 was relatively small because the gaseous reaction product at a high temperature was supplied to the stripper 10, but isopropyl alcohol and water included in the first discharge stream were discharged in a gaseous state to the upper portion of the stripper because the first discharge stream was introduced in a gaseous stage to the stripper without being condensed. In addition, isopropyl alcohol and water included in the second discharge stream did not pass through the rectifying unit because the second discharge stream was supplied to the first stage of the stripper 10, and thus, most of them were discharged to the upper portion. That is, in Comparative Example 2, it was impossible to perform separation into isopropyl alcohol with water and the propylene monomer using the stripper 10 because isopropyl alcohol was not discharged to the lower portion of the stripper 10, and a temperature sufficient for cooling the first discharge stream by heat exchange using the lower discharge stream was not able to be implemented because the temperature was raised with the increase in the water content.

The invention claimed is:

1. A method of preparing isopropyl alcohol, the method comprising:
   supplying a feed stream including a propylene monomer and water to a reaction unit;
   reacting the propylene monomer and water to produce a reaction product including isopropyl alcohol, the propylene monomer, and water;
   separating the reaction product into a first discharge stream including a gaseous reaction product and a second discharge stream including a liquid reaction product;
   supplying the first discharge stream and the second discharge stream to a stripper, respectively; and
   circulating an upper discharge stream including the propylene monomer from the stripper to the reaction unit and supplying a lower discharge stream including water and isopropyl alcohol from the stripper to an isopropyl alcohol purification unit,
   wherein the first discharge stream is condensed by a first heat exchanger and supplied as a liquid phase to the stripper.

2. The method of claim 1, wherein a temperature of the first discharge stream and the second discharge stream is 105° C. to 150° C.

3. The method of claim 2, wherein the temperature of the first discharge stream and the second discharge stream is 115° C. to 140° C.

4. The method of claim 1,
wherein the first discharge stream comprises the propylene monomer in an amount of 85 wt % to 95 wt %, and
wherein the second discharge stream comprises the propylene monomer in an amount of 1 wt % to 10 wt %.

5. The method of claim 1, wherein an amount of isopropyl alcohol included in the second discharge stream is higher than an amount of isopropyl alcohol included in the first discharge stream.

6. The method of claim 1,
wherein the first discharge stream is supplied to an upper part of the stripper, and
wherein the second discharge stream is supplied to the stripper at a position lower than the upper part of the stripper to which the first discharge stream is supplied.

7. The method of claim 6,
wherein the first discharge stream is supplied to a first stage of the stripper, and
wherein the second discharge stream is supplied to a stage positioned at 10% to 50% of a theoretical number of stages of the stripper.

8. The method of claim 7, wherein the second discharge stream is supplied to a stage positioned at 15% to 35% of the theoretical number of stages of the stripper.

9. The method of claim 1, wherein a portion of the upper discharge stream from the stripper is supplied to an inert gas removal unit to remove an inert gas component and then circulated to the reaction unit.

10. The method of claim 1,
wherein the reaction unit includes a reactor and one or more second heat exchangers,
a feed stream is supplied to the reactor to perform a reaction and a gaseous reaction product is formed, and
the gaseous reaction product stream discharged from the reactor is separated into the first discharge stream including the gaseous reaction product and the second discharge stream including a liquid reaction product while passing through one or more second heat exchangers, which are supplied to the stripper, respectively.

11. The method of claim 1, the method further comprising exchanging heat between the first discharge stream and a portion of the lower discharge stream in the first heat exchanger.

* * * * *